(12) United States Patent
Takeda

(10) Patent No.: US 6,768,027 B2
(45) Date of Patent: Jul. 27, 2004

(54) CINNAMALDEHYDE COMPOUND HAVING AN AZIDO GROUP

(75) Inventor: Mineko Takeda, Inba-gun (JP)

(73) Assignee: Toyo Gosei Kogyo Co. Ltd., Chiba (JP)

( * ) Notice: Subject to any disclaimer, the term of this patent is extended or adjusted under 35 U.S.C. 154(b) by 0 days.

(21) Appl. No.: 10/400,838

(22) Filed: Mar. 27, 2003

(65) Prior Publication Data
US 2003/0191329 A1 Oct. 9, 2003

(30) Foreign Application Priority Data
Mar. 29, 2002 (JP) ........................ 2002-097970

(51) Int. Cl.⁷ .................. C07C 47/52; C07C 245/00; C09B 29/00
(52) U.S. Cl. ................ 568/425; 534/730; 534/885
(58) Field of Search ................ 568/425; 534/730, 534/885

(56) References Cited

U.S. PATENT DOCUMENTS

| | | | |
|---|---|---|---|
| 2,948,610 A | | 8/1960 | Merrill et al. |
| 3,598,844 A | * | 8/1971 | Ruckert et al. ........... 260/349 |
| 3,695,886 A | | 10/1972 | Clecak et al. |
| 3,749,713 A | | 7/1973 | Clecak et al. |
| 4,241,162 A | * | 12/1980 | Hatano et al. ........... 430/195 |
| 4,588,669 A | | 5/1986 | Asano |
| 4,728,594 A | | 3/1988 | Nonogaki et al. |

FOREIGN PATENT DOCUMENTS

| | | |
|---|---|---|
| GB | 892 811 | 3/1962 |
| JP | 50141403 | 11/1975 |
| JP | 51 001443 | 1/1976 |
| JP | 51 001444 | 1/1976 |
| JP | 52 103201 | 8/1977 |
| JP | 59 193859 | 3/1988 |
| JP | 63 227556 | 9/1988 |
| JP | 07 234504 | 9/1995 |
| JP | 09 068796 | 3/1997 |
| JP | 63 132235 | 6/1998 |

OTHER PUBLICATIONS

Youhui et al., A Novel Photopolymer with Improved Sensitivity Speed and Stability, Journal of Xi'an Jiaotong University, vol. 32, No. 8. (Aug. 1998).

* cited by examiner

Primary Examiner—James O. Wilson
Assistant Examiner—Sikarl A. Witherspoon
(74) Attorney, Agent, or Firm—Huntley & Associates LLC

(57) ABSTRACT

The invention provides a novel azidocinnamaldehyde compound which, when used as an intermediate for providing a photosensitive moiety of a photoresist, introduces a photosensitive moiety having high sensitivity and attaining high contrast between the exposed portion and the unexposed portion, and which per se can serve as a photosensitive moiety. The azidocinnamaldehyde compound is represented by formula(I):

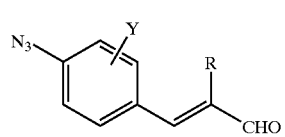

(1)

wherein R represents a lower alkyl group and Y represents hydrogen or a sulfonate salt group.

3 Claims, No Drawings

CINNAMALDEHYDE COMPOUND HAVING AN AZIDO GROUP

BACKGROUND OF THE INVENTION

1. Field of the Invention

The present invention relates to a novel cinnamaldehyde compound having an azido group. The compound is useful as an intermediate for providing a photosensitive moiety of a photoresist, and also as the photosensitive moiety.

2. Description of the Related Art

Azide-based photoresists find a variety of uses, by virtue of offering a wide range of adaptability, low cost, and high resolution.

Among azide compounds conventionally used for providing such photoresists, disodium 4,4'-diazidostilbene-2,2'-disulfonate is known to be a typical azide compound.

Photoresists produced from such an azide compound show remarkably high sensitivity to light of a wavelength of 300 to 360 nm. However, in order to further enhance sensitivity of photoresists, an azide compound showing its light absorption band in a longer wavelength region has been desired.

In this connection, there have been proposed water-soluble diazide compounds which are synthesized through condensation of, for example, sodium 4-azidobenzaldehyde-2-sulfonate with an aliphatic ketone such as acetone or cyclohexanone. For example, Japanese Patent Application Laid-Open (kokai) No. 50-141403 discloses a diazide compound showing its light absorption band in a longer wavelength region.

Although the above-mentioned conventional water-soluble diazide compounds show their light absorption band which is red-shifted by reacting an azidobenzaldehyde compound with an aliphatic ketone or a similar compound, there has still remained a demand for further red-shifting the light absorption band.

Azidobenzaldehyde compounds, which are employed as raw materials for introducing a photosensitive unit to a variety of compounds, show its absorption maximum wavelength at about 290 nm. Since the wavelength range of the light absorption band of the introduced photosensitive unit is varied in accordance with the absorption maximum wavelength of the employed azidobenzaldehyde compound, the obtained wavelength region of the light absorption band is still unsatisfactory. Thus, a need exists to introduce a photosensitive unit showing its light absorption band in a further red-shifted wavelength region.

SUMMARY OF THE INVENTION

In view of the foregoing, the present inventor has carried out extensive studies on provision of a novel aldehyde compound having an azido group (hereinafter may be referred to as a novel azidoaldehyde compound), which compound, when used as an intermediate for providing a photosensitive moiety of a photoresist, introduces a photosensitive moiety having high sensitivity and attaining high contrast between the exposed portion and the unexposed portion, and which compound per se can also serve as a photosensitive moiety. The inventor has found that the aforementioned problems can be solved by an azidocinnamaldehyde compound produced through insertion of a double bond into an azidobenzaldehyde compound. The present invention has been accomplished on the basis of this finding.

Thus, an object of the present invention is to provide a novel azidocinnamaldehyde compound which can readily provide a photosensitive unit showing its light absorption band in a longer wavelength region.

Accordingly, the present invention provides an azidocinnamaldehyde compound represented by the following formula (I):

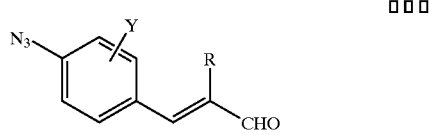

wherein R represents a lower alkyl group such as a C1 to C4 alkyl group, preferably a linear-chain group, more preferably a methyl group or an ethyl group.

In formula (I), Y represents hydrogen or a sulfonate salt group. Here, a sulfonate salt group is represented by $-SO_3M$, and M represents an alkali metal such as lithium, sodium, or potassium; or an ammonium compound such as ammonium, monoalkylammonium, dialkylammonium, trialkylammonium, or tetraalkylammonium, for example.

DETAILED DESCRIPTION OF PREFERRED EMBODIMENTS

The novel azidocinnamaldehyde compound overcomes the aforementioned drawbacks of conventional azidobenzaldehyde compounds. Thus, when used as an intermediate for providing a photosensitive moiety of a photoresist, the compound introduces a photosensitive moiety having high sensitivity and attaining high contrast between the exposed portion and the unexposed portion, and the compound per se can serve as a photosensitive moiety.

The azidocinnamaldehyde compound of the present invention can be produced through, for example, condensation of an azidobenzaldehyde compound (II) with a lower alkylaldehyde (III) in accordance with the following reaction scheme.

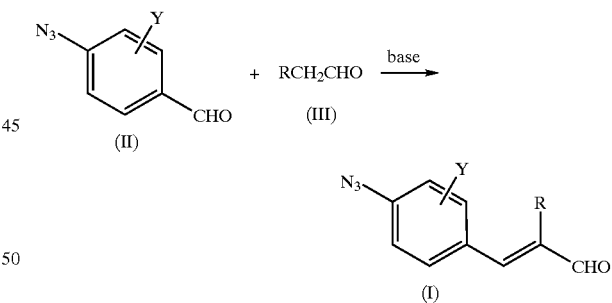

Examples of the azidobenzaldehyde compound (II) employed in the above reaction include 4-azidobenzaldehyde and sodium 4-azidobenzaldehyde-2-sulfonate. Examples of the lower alkylaldehyde (III) include propanal and butanal. Use of acetaldehyde is not preferred, since yield of the target product decreases considerably.

In one embodiment, the reaction represented by the above reaction scheme is carried out in a solvent mixture of water and a lower alcohol such as ethanol or isopropyl alcohol and in the presence of a base such as potassium hydroxide or sodium hydroxide. However, no particular limitation is imposed on the reaction conditions, and those generally employed for condensation reaction of carbonyl compounds can also be employed.

The thus-obtained azidocinnamaldehyde compound of the present invention represented by formula (I) is a novel compound which no literature has reported. The azidocinnamaldehyde compound shows its absorption maximum wavelength which is red-shifted as compared with that of the starting azidobenzaldehyde compound.

Accordingly, when the azidocinnamaldehyde compound of the present invention is used instead of a conventional azidobenzaldehyde compound for providing a corresponding photosensitive unit of a photoresist, a photosensitive compound showing its absorption maximum wavelength in a longer wavelength region can be produced.

EXAMPLES

The present invention will next be described in detail by way of examples, which should not be construed as limiting the invention thereto.

Example 1

4-Azidobenzaldehyde (29.42 g, 0.2 mol) and propionaldehyde (12.22 g, 0.2 mol) were dissolved in a solvent mixture of isopropyl alcohol (100 g) and pure water (50 g). Under cooling in an ice bath, sodium hydroxide (2 g) dissolved in pure water (20 g) was added to the solution, and the mixture was stirred for two hours. Propionaldehyde (12.22 g, 0.2 mol) was added again to the mixture, and the resultant mixture was stirred for a further three hours. The formed precipitates were collected through filtration and dried, to thereby yield 23.14 g of p-azido-2-methylcinnamaldehyde as yellow crystals (yield: 62%). The compound thus obtained was identified on the basis of the $^1$H-NMR measurements shown in Table 1.

TABLE 1

| ppm | type | H | J value |
|---|---|---|---|
| 9.57 | s | 1H | |
| 7.55 | d | 2H | 8.6 |
| 7.22 | s | 1H | |
| 7.11 | d | 2H | 8.5 |
| 2.08 | s | 3H | |

Example 2

The procedure of Example 1 was repeated, except that propionaldehyde (12.22 g) was replaced by butylaldehyde (14.42 g), to thereby yield 10.27 g of p-azido-2-ethylcinnamaldehyde (yield: 51%). The compound thus obtained was identified on the basis of the $^1$H-NMR measurements shown in Table 2.

TABLE 2

| ppm | type | H | J value |
|---|---|---|---|
| 9.53 | s | 1H | |
| 7.52 | d | 2H | 8.4 |
| 7.15 | s | 1H | |
| 7.11 | d | 2H | 8.4 |
| 2.56 | q | 2H | 7.6 |
| 1.12 | t | 3H | 7.6 |

Example 3

Sodium 4-azido-2-sulfobenzaldehyde (12.26 g, 0.05 mol) was dissolved in a solvent mixture of isopropyl alcohol (50 g) and pure water (25 g). Sodium hydroxide (1 g) dissolved in pure water (10 g) was added to the solution, and the mixture was cooled in an ice bath. Propionaldehyde (3.06 g, 0.05 mol) was added to the mixture, and the resultant mixture was stirred for two hours. Subsequently, propionaldehyde (3.06 g, 0.05 mol) was again added to the mixture, and the resultant mixture was stirred for a further three hours. The formed precipitates were collected through filtration and dried, to thereby yield 6.11 g of 1-(Sodium 4-azido-2-sulfophenyl)-2-methyl-propenaldehyde as pale yellow crystals (yield: 42%). The compound thus obtained was identified on the basis of the $^1$H-NMR measurements shown in Table 3.

TABLE 3

| ppm | type | H | J value |
|---|---|---|---|
| 9.11 | s | 1H | |
| 7.58 | d | 1H | 0.8 |
| 7.18 | d | 1H | 2.4 |
| 7.11 | d | 1H | 8.4 |
| 6.84 | dd | 1H | 2.4, 8.4 |
| 1.43 | d | 3H | 1.6 |

Comparative Example 1

4-Azidobenzaldehyde (14.71 g, 0.1 mol) was dissolved in a solvent mixture of isopropyl alcohol (50 g) and pure water (15 g). Under cooling in an ice bath, sodium hydroxide (1 g) dissolved in pure water (10 g) was added to the solution, and the resultant mixture was stirred for ten minutes. Acetaldehyde (4.41 g, 0.1 mol) was added to the mixture, and the resultant mixture was stirred for two hours at the same temperature. Subsequently, acetaldehyde (4.41 g, 0.1 mol) was again added to the mixture, and the resultant mixture was stirred for a further three hours. The formed precipitates were collected through filtration and dried, to thereby yield 4.82 g of p-azido-cinnamaldehyde as brown solid (yield: 28%) as a mixture containing acetaldehyde (2.7%).

Application Example 1

By use of p-azido-2-methylcinnamaldehyde which had been synthesized in Example 1, a bisazide compound was yielded in the following manner. p-Azido-2-methylcinnamaldehyde (4.68 g) was dissolved in ethanol (25 g), and a 25% aqueous sodium hydroxide solution (2.5 g) was added to the ethanol solution. The mixture was stirred for ten minutes, followed by addition of acetone (0.73 g) thereto. The resultant mixture was stirred for two hours at 30° C. The formed precipitates were collected through filtration and dried, to thereby yield 4.13 g of 2,8-di-(4'-azidobenzal)nona-3,6-dien-5-one as yellow solid (yield: 76%)

The thus-obtained bisazide compound was found to show its absorption maximum wavelength ($\lambda_{max}$) at 373 nm, which is red-shifted as compared with the absorption maximum wavelength ($\lambda_{max}$=358 nm) of the bisazide compound which had been synthesized from p-azidobenzaldehyde instead of p-azido-2-methylcinnamaldehyde.

Application Example 2

By use of p-azido-2-methylcinnamaldehyde (α-methylazidocinnamaldehyde) which had been synthesized in Example 1, an azlactone compound was yielded in the following manner.

Hippuric acid (17.9 g), α-methylazidocinnamaldehyde (18.7 g), acetic anhydride (30 g), sodium acetate (1.0 g), toluene (25 g), and acetonitrile (20 g) were mixed together, and the mixture was heated at 60° C. for 24 hours, and subsequently allowed to cool. Sixteen hours after the start of cooling, the mixture was filtered at room temperature. The solid remaining on the filter was washed with cold methanol (40 g) and dried under reduced pressure, to thereby yield 23 g of an azlactone compound having an azido group; i.e., 4-(4-azido-β-methyl-cinnamylidene)-2-phenyl-2-oxazolin-5-one.

The thus-obtained azlactone compound was found to show its absorption maximum wavelength at 398 nm. The azlactone compound was dispersed in THF (230 g), and aminobutylaldehyde dimethylacetal (10 g) was gradually added to the dispersion at 5 to 10° C. Two hours after addition, the reaction mixture showed a new absorption at 328 nm, whereas the absorption at 398 nm disappeared. Subsequently, the reaction mixture was added to water (345 g), followed by stirring for two hours. The thus-formed precipitates were collected through filtration, to thereby yield 29 g of 5-(4-azidophenyl)-N-(4,4-dimethoxybutyl)-4-methyl-2-phenylcarbonylamino-penta-2,4-dienamide.

The thus-obtained compound was found to show its absorption maximum wavelength at 328 nm, which is longer than the absorption maximum wavelength (310 nm) of the azlactone compound of Comparative Application Example 1 (obtained from azidobenzaldehyde instead of α-methylazidocinnamaldehyde), which will be described hereinbelow.

Application Example 3

By use of p-azido-2-methylcinnamaldehyde (α-methylazidocinnamaldehyde) which had been synthesized in Example 1, an azlactone compound was yielded in the following manner.

Nicotinoylglycine (18 g), α-methylazidocinnamaldehyde (18.7 g), acetic anhydride (30 g), sodium acetate (1.0 g), cyclohexane (30 g), and acetonitrile (10 g) were mixed together, and the mixture was heated at 60° C. for 24 hours, and subsequently allowed to cool. And IPA (30 g) was added to the mixture. After sixteen hours, the mixture was filtered at room temperature. The solid remaining on the filter was washed with cold methanol (40 g) and dried under reduced pressure, to thereby yield 18 g of an azlactone compound having an azido group; i.e., 4-(4-azido-β-methyl-cinnamylidene)-2-(3-pyridyl)-2-oxazolin-5-one.

The azlactone compound was found to show its absorption maximum wavelength at 401 nm. The thus-obtained azlactone compound was dispersed in THF (230 g), and aminobutylaldehyde dimethylacetal (10 g) was gradually added to the dispersion at 5 to 10° C. Two hours after addition, the reaction mixture showed a new absorption at 323 nm, whereas the absorption at 401 nm disappeared. Subsequently, water (49.5 g) was added to the reaction mixture, followed by stirring for two hours. The thus-formed precipitates were collected through filtration, to thereby yield 27 g of 5-(4-azidophenyl)-N-(4,4-dimethoxybutyl)-4-methyl-2-((3-pyridyl)carbonylamino)-penta-2,4-dienamide.

The thus-obtained compound was found to show its absorption maximum wavelength at 323 nm, which is longer than the absorption maximum wavelength (310 nm) of the azlactone compound of Comparative Application Example 2 (obtained from azidobenzaldehyde instead of α-methylazidocinnamaldehyde), which will be described hereinbelow.

Comparative Application Example 1

Hippuric acid (17.9 g), azidobenzaldehyde (15 g), acetic anhydride (20 g), sodium acetate (1.0 g), toluene (25 g), and acetonitrile (20 g) were mixed together, and the mixture was heated at 70° C. for 6 hours, and subsequently allowed to cool. Sixteen hours after the start of cooling, the mixture was filtered at room temperature. The solid remaining on the filter was washed with cold methanol (40 g) and dried under reduced pressure, to thereby yield 17 g of an azlactone compound having an azido group; i.e., 4-((4-azidophenyl)methylene)-2-phenyl-1,3-oxazolin-5-one.

The thus-obtained azlactone compound was found to show its absorption maximum wavelength at 390 nm. The azlactone compound was dispersed in THF (150 g), and aminobutylaldehyde dimethylacetal (8.6 g) was gradually added to the dispersion at 5 to 10° C. Two hours after addition, the reaction mixture showed a new absorption at 310 nm, whereas the absorption at 390 nm disappeared. Water (500 g) was added to the reaction mixture, followed by stirring for two hours. The thus-formed precipitates were collected through filtration, to thereby yield 18 g of 3-(4-azidophenyl)-N-(4,4-dimethoxybutyl)-2-phenylcarbonylamino-prop-2-enamide.

Comparative Application Example 2

Nicotinoylglycine (18.0 g), azidobenzaldehyde (15 g), acetic anhydride (30 g), sodium acetate (1.0 g), and cyclohexane (30 g) were mixed together, and the mixture was heated at 70° C. for 6 hours, and subsequently allowed to cool. Sixteen hours after the start of cooling, IPA (30 g) was added to the mixture, and the mixture was filtered at room temperature. The solid remaining on the filter was washed with cold methanol (30 g) and dried under reduced pressure, to thereby yield 10 g of an azlactone compound having an azido group; i.e., 4-((4-azidophenyl)methylene)-2-(3-pyridyl)-1,3-oxazolin-5-one.

The azlactone compound was found to show its absorption maximum wavelength at 390 nm. The thus-obtained azlactone compound was dispersed in IPA (55 g), and aminobutylaldehyde dimethylacetal (4.6 g) was gradually added to the dispersion at 5 to 10° C. Two hours after addition, the reaction mixture showed a new absorption at 310 nm, whereas the absorption at 390 nm disappeared. Subsequently, water (500 g) was added to the reaction mixture, and pH of the mixture was adjusted to 8.0 by use of aqueous ammonia, followed by stirring for two hours at 5° C. The thus-formed precipitates were collected through filtration, to thereby yield 6 g of 3-(4-azidophenyl)-N-(4,4-dimethoxybutyl)-2-((3-pyridyl)carbonylamino)-prop-2-enamide.

As described hereinabove, the present invention provides a novel azidocinnamaldehyde compound prepared through insertion of a double bond into an azidobenzaldehyde compound. The compound of the present invention can readily provide a photosensitive unit showing its light absorption band in a long wavelength region.

What is claimed is:

1. A cinnamaldehyde compound having an azido group represented by formula(I):

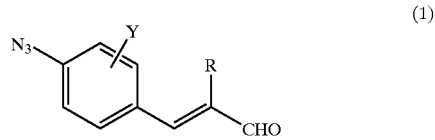

(1)

wherein R represents a lower alkyl group and Y represents hydrogen or a sulfonate salt group.

2. A cinnamaldehyde compound having an azido group according to claim 1, wherein R is a methyl group or an ethyl group.

3. A cinnamaldehyde compound having an azido group according to claim 1 or 2, wherein Y is a sulfonate salt group.

* * * * *